US006444235B1

(12) United States Patent
Ebner

(10) Patent No.: US 6,444,235 B1
(45) Date of Patent: Sep. 3, 2002

(54) CANELO PRODUCTS AND METHODS OF MAKING AND USING SAME

(75) Inventor: Raquel Alvarez Ebner, Aysen (CL)

(73) Assignee: bioActiva microtechne, Lonetree, CO (US)

( * ) Notice: Subject to any disclaimer, the term of this patent is extended or adjusted under 35 U.S.C. 154(b) by 0 days.

(21) Appl. No.: 09/684,003

(22) Filed: Oct. 6, 2000

Related U.S. Application Data

(60) Provisional application No. 60/157,915, filed on Oct. 6, 1999.

(51) Int. Cl.$^7$ ................................................ A61K 35/78
(52) U.S. Cl. ........................................ 424/725; 424/769
(58) Field of Search .................... 424/725, 65

(56) References Cited

U.S. PATENT DOCUMENTS 4,927,850 A    5/1990  Bayless et al. ............. 514/458
5,707,611 A  * 1/1998  Ikemura et al.

FOREIGN PATENT DOCUMENTS

DE    1971-60393 S  *  6/1969
JP       55153780 A  * 11/1980

OTHER PUBLICATIONS

Products Chilean, 2000, p. 1—3 http://www.finext.cl/ProducChi__i.htm.*

PDR for Herbal Medicines, Medical Economics Company, 1998, p. 813–814.*

Tomas M., Canelo, 1998, pp. 1–4, http://www.nido.cl/studpages/midd/chiflr/canelo.html.*

Cechinel et al., "Isolation and Identification of active compounds from Drimys winteri barks", J. of Ethnopharmocology, Oct. 1998, vol. 62, No. 3, pp. 223–227—abstract.*

Sayah et al., *Gen. Pharmac*, vol. 28, No. 5, pp. 699–704 (1997).

Tratsk et al., *Inflamm. Res.*, 46, pp. 509–514 (1997).

* cited by examiner

Primary Examiner—Leon B. Lankford, Jr.
Assistant Examiner—Ruth A. Davis
(74) Attorney, Agent, or Firm—Sheridan Ross P.C.

(57) ABSTRACT

Extracts of the Canelo tree are prepared and used to cleanse wounds, to act as an anti-rheumatic, anti-ulceretic, to eliminate body odors, treat chronic infections, as a natural flavor extract, as a pest repellancy agent and as a phyto nutrient. Such extract has therapeutic uses including the treatment of pancreatic cancer and the treatment of fungal, yeast and bacterial infections. The significant concentrations of bioflavinoids in Canelo tree extract makes such extract particularly useful in the maintenance of normal blood vessel conditions and as a protectorant of capillaries. A synergistic effect is apparent in a mixture of ascorbic acid and Canelo tree extract. Canelo tree extract also contains Sesamin and is therefore useful as an insect repellant, particularly when incorporated into building materials to protect such materials against undesired infestation by insects.

2 Claims, 21 Drawing Sheets

Table 1: Constituents of Canelo "young" bark oil

| Peak # | η | Area % | Compound |
|---|---|---|---|
| 1 | 11.83 | 9.14 | alpha-Pinene |
| 3 | 12.83 | 1.66 | beta-Pinene |
| 6 | 13.82 | 8.96 | Limonene |
| 13 | 17.43 | 2.13 | Linalool |
| 16 | 18.35 | 0.62 | Unk |
| 17 | 18.59 | 1.39 | beta-caryophyllene |
| 20 | 19.20 | 1.44 | 1-alpha-Terpineol |
| 28 | 22.23 | 2.31 | Farnesol |
| 30 | 23.13 | 14.31 | Elemol |
| 31 | 23.89 | 2.26 | unk |
| 32 | 24.03 | 2.28 | unk |
| 33 | 24.21 | 1.30 | unk/MW 216 |
| 34 | 24.42 | 6.95 | gamma-Maallene |
| 35 | 24.67 | 0.98 | Calarene |
| 36 | 24.78 | 0.50 | unk |
| 39 | 26.32 | 12.79 | Eudesmol |
| 40 | 25.52 | 10.77 | Beta-Eudesmol |
| 50 | 31.01 | 17.66 | Driminol |

FIG. 2

Table 2: Constituents of Canelo "old" bark oil

| Peak # | η | Area % | Compound |
|---|---|---|---|
| 4 | 11.79 | 2.72 | alpha-Pinene |
| 6 | 12.77 | 1.81 | Gamma-3-Carene |
| 17 | 17.77 | 1.20 | unk |
| 18 | 18.04 | 9.24 | unk |
| 19 | 18.19 | 15.32 | unk |
| 20 | 18.33 | 2.00 | unk |
| 21 | 18.56 | 3.26 | beta-Caryophyllene |
| 22 | 18.70 | 3.62 | alpha-Humulene |
| 23 | 18.85 | 2.37 | unk |
| 24 | 19.14 | 8.09 | beta-Himachalene |
| 25 | 19.49 | 2.04 | trans bala-Farnesene |
| 26 | 19.60 | 6.37 | alpha-Beramotene |
| 27 | 19.76 | 1.17 | unk |
| 28 | 19.94 | 7.97 | Benzene 1-(1,5dimethyl-4-hexenyl)-4-Methyl |
| 33 | 22.01 | 0.78 | unk |
| 34 | 22.18 | 0.48 | unk |
| 37 | 33.07 | 2.30 | elemol |
| 38 | 23.19 | 0.55 | beta-Bisabolene |
| 42 | 23.83 | 1.11 | unk |
| 43 | 23.92 | 6.21 | unk |
| 45 | 24.17 | 1.98 | beta-Himachalene |
| 46 | 24.38 | 1.23 | gamma-Maaliene |
| 47 | 14.67 | 2.33 | unk |
| 49 | 26.25 | 0.87 | unk |
| 50 | 25.46 | 0.93 | beta-Eudesmol |
| 51 | 26.92 | 8.14 | unk |
| 67 | 30.94 | 2.75 | Driminol |

*FIG. 3*

Table 3: Constituent comparison of bark oils.

| young bark | | | old bark | | | Compound |
|---|---|---|---|---|---|---|
| peak # | η | Area % | peak # | η | Area % | |
| 1 | 11.83 | 9.14 | 4 | 11.72 | 2.72 | alpha-Pinene |
| 2 | 12.83 | 1.68 | 6 | 12.77 | 1.81 | beta-Pinane/gamma-3-Carene |
| 6 | 13.82 | 8.96 | | | | Limonene |
| 13 | 17.43 | 2.13 | | | | Linalool |
| | | | 17 | 17.77 | 1.20 | unk |
| | | | 18 | 18.04 | 9.24 | unk |
| | | | 19 | 18.19 | 15.32 | unk |
| 16 | 18.35 | 0.62 | 20 | 18.33 | 2.00 | unk |
| 17 | 18.59 | 1.39 | 21 | 18.58 | 3.26 | beta-Caryophyllene |
| | | | 22 | 18.70 | 3.62 | alpha-Humulene |
| | | | 23 | 18.85 | 2.37 | unk |
| | | | 24 | 19.14 | 8.09 | beta-Himachalene |
| 20 | 19.20 | 1.44 | | | | 1-alpha-Torpineol |
| | | | 25 | 19.49 | 2.04 | trans-beta-Terpineol |
| | | | 26 | 19.50 | 5.37 | alpha-Bergamotene |
| | | | 27 | 19.76 | 1.17 | unk |
| | | | 28 | 19.94 | 7.97 | Benzene, 1-(1,5, dimethyl-4-hexenyl)-4-methyl |
| | | | 33 | 22.01 | 0.78 | unk |
| 28 | 22.23 | 2.31 | 34 | 22.18 | 0.48 | Farsenollunk |
| 30 | 23.13 | 14.31 | 37 | 23.07 | 2.30 | Elemol |
| | | | 38 | 23.19 | 0.55 | beta-Hiaebolene |
| 31 | 23.89 | 2.26 | 42 | 23.83 | 1.11 | unk |
| 32 | 24.03 | 2.28 | 43 | 23.92 | 6.21 | unk |
| 33 | 24.21 | 1.30 | 45 | 24.17 | 1.98 | Beta-Himachalene/ mw 218 |
| 34 | 24.42 | 5.95 | 48 | 24.38 | 1.23 | Gamma-Maaliene |
| | | | 47 | 24.87 | 2.33 | unk |
| 35 | 24.67 | 0.98 | | | | Calarene |
| 38 | 24.78 | 0.50 | | | | unk |
| 39 | 25.32 | 12.79 | 49 | 25.25 | 0.87 | Eudesmol/unk |
| 40 | 25.52 | 10.77 | 50 | 25.46 | 0.93 | beta-Eudesmol |
| | | | 51 | 25.92 | 8.14 | unk |
| 50 | 31.01 | 1.7.66 | 57 | 30.94 | 2.75 | Drimnol |

*FIG. 4*

Constituents of Canelo Oil

| Peak # | η | Area % | Compound |
|---|---|---|---|
| 4 | 11.79 | 2.72 | alpha-Pinene |
| 6 | 12.77 | 1.81 | Gamma-3-Carene |
| 17 | 17.77 | 1.20 | unk |
| 18 | 18.04 | 9.24 | unk |
| 19 | 18.19 | 15.32 | unk |
| 20 | 18.33 | 2.00 | unk |
| 21 | 18.56 | 3.26 | beta-Caryophyllene |
| 22 | 18.70 | 3.62 | alpha-Humulene |
| 23 | 18.85 | 2.37 | unk |
| 24 | 19.14 | 8.09 | beta-Himachalene |
| 25 | 19.49 | 2.04 | trans bala-Famesene |
| 26 | 19.60 | 6.37 | alpha-Beramotene |
| 27 | 19.76 | 1.17 | unk |
| 28 | 19.94 | 7.97 | Benzene 1-(1,5dimethyl-4-hexenyl)-4-Methyl |
| 33 | 22.01 | 0.78 | unk |
| 34 | 22.18 | 0.48 | unk |
| 37 | 33.07 | 2.30 | elemol |
| 38 | 23.19 | 0.55 | beta-Bisabolene |
| 42 | 23.83 | 1.11 | unk |
| 43 | 23.92 | 6.21 | unk |
| 45 | 24.17 | 1.98 | beta-Himachalene |
| 46 | 24.38 | 1.23 | gamma-Maaliene |
| 47 | 14.67 | 2.33 | unk |
| 49 | 26.25 | 0.87 | unk |
| 50 | 25.46 | 0.93 | beta-Eudesmol |
| 51 | 26.92 | 8.14 | unk |
| 67 | 30.94 | 2.75 | Driminol |

*FIG. 6*

LC/MS Analysis of Old Canelo Bark Extracts

| Extract | Yield (w/w%) | Major Constituents | | | |
|---|---|---|---|---|---|
| | | Retention Time (min) | % Abundance | Mol. Weight | Name/ Identify |
| Hexane | 5.5 | 21.38 | 82.6 | 234 | "Canelo 1" |
| | | 22.61 | 7.1 | 426 | "Canelo 2" |
| Ethyl Acetate | 3.6 | 11.95 | 3.3 | 412 | "Canelo 3" |
| | | 19.55 | 1.1 | 396 | "Canelo 4" |
| | | 21.2 | 50.8 | 234 | "Canelo 1" |
| | | 22.6 | 35.8 | 426 | "Canelo 2" |
| Methanol | 13.8 | 5.55 | 8 | 578 | "Canelo 5" |
| | | 6.59 | 7.3 | 578 | "Canelo 6" |
| | | 7.35 | 9.1 | 290 | "Canelo 7" |
| | | 15.8 | 37.5 | 450 | "Canelo 8" |

FIG. 7

LC/MS Analysis of Young Canelo Bark Extracts

| Extract | Yield (w/w%) | Major Constituents | | | |
|---|---|---|---|---|---|
| | | Retention Time (min) | % Abundance | Mol. Weight | Name/ Identify |
| Hexane | 4.4 | 21.53 | 82.0 | 234 | "Canelo 1" |
| | | 42.27 | 7.6 | 368 | "Canelo 9" |
| Ethyl Acetate | 4.9 | 12.29 | 15.7 | 412 | "Canelo 3" |
| | | 20.99 | 72.5 | 396, 234 | "Canelo 4" "Canelo 1" |
| Methanol | 10.5 | 5.68 | 10.9 | 578 | "Canelo 5" |
| | | 6.55 | 16.4 | 578 | "Canelo 6" |
| | | 7.37 | 14.3 | 290 | "Canelo 7" |

FIG. 8

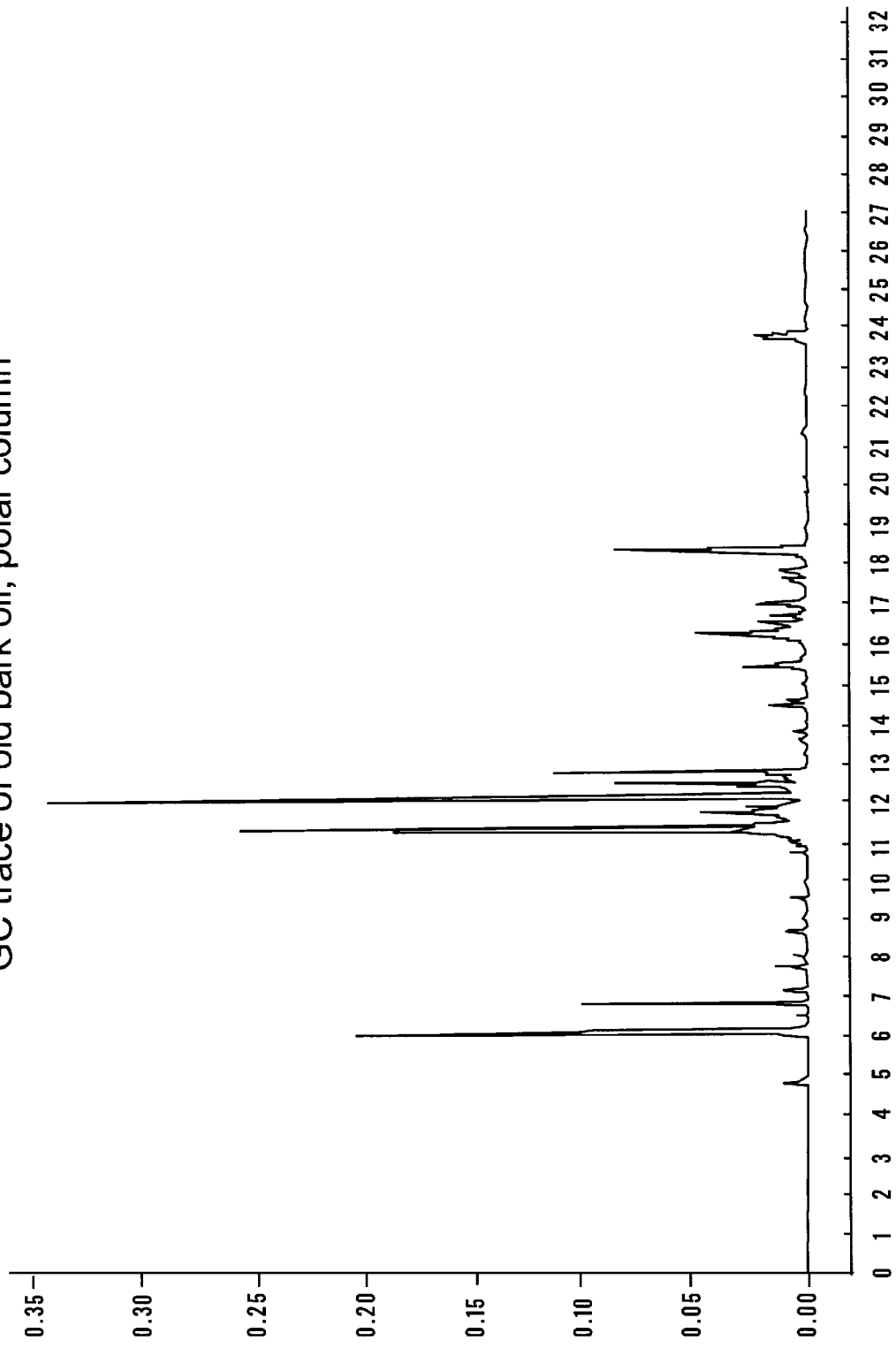

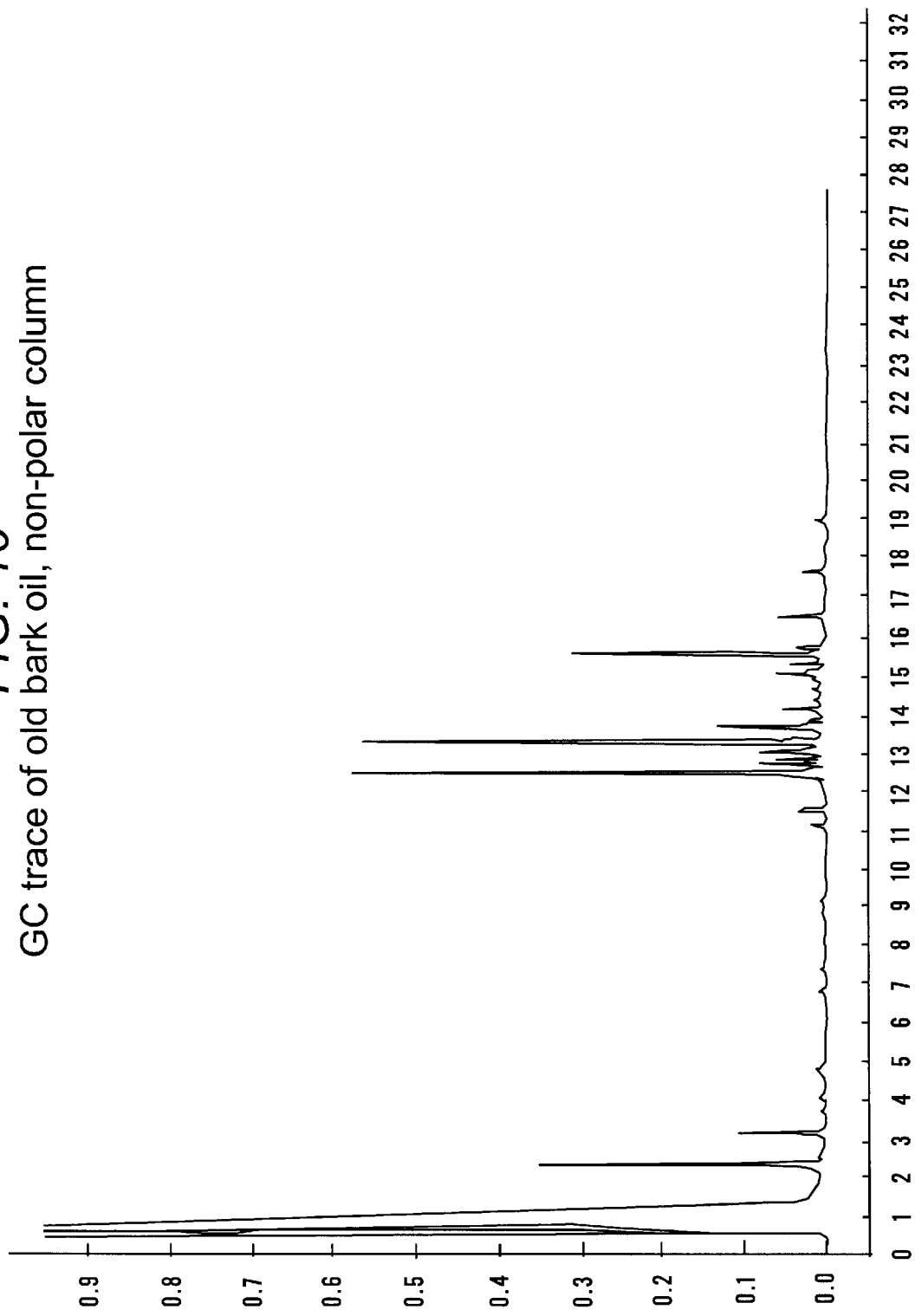

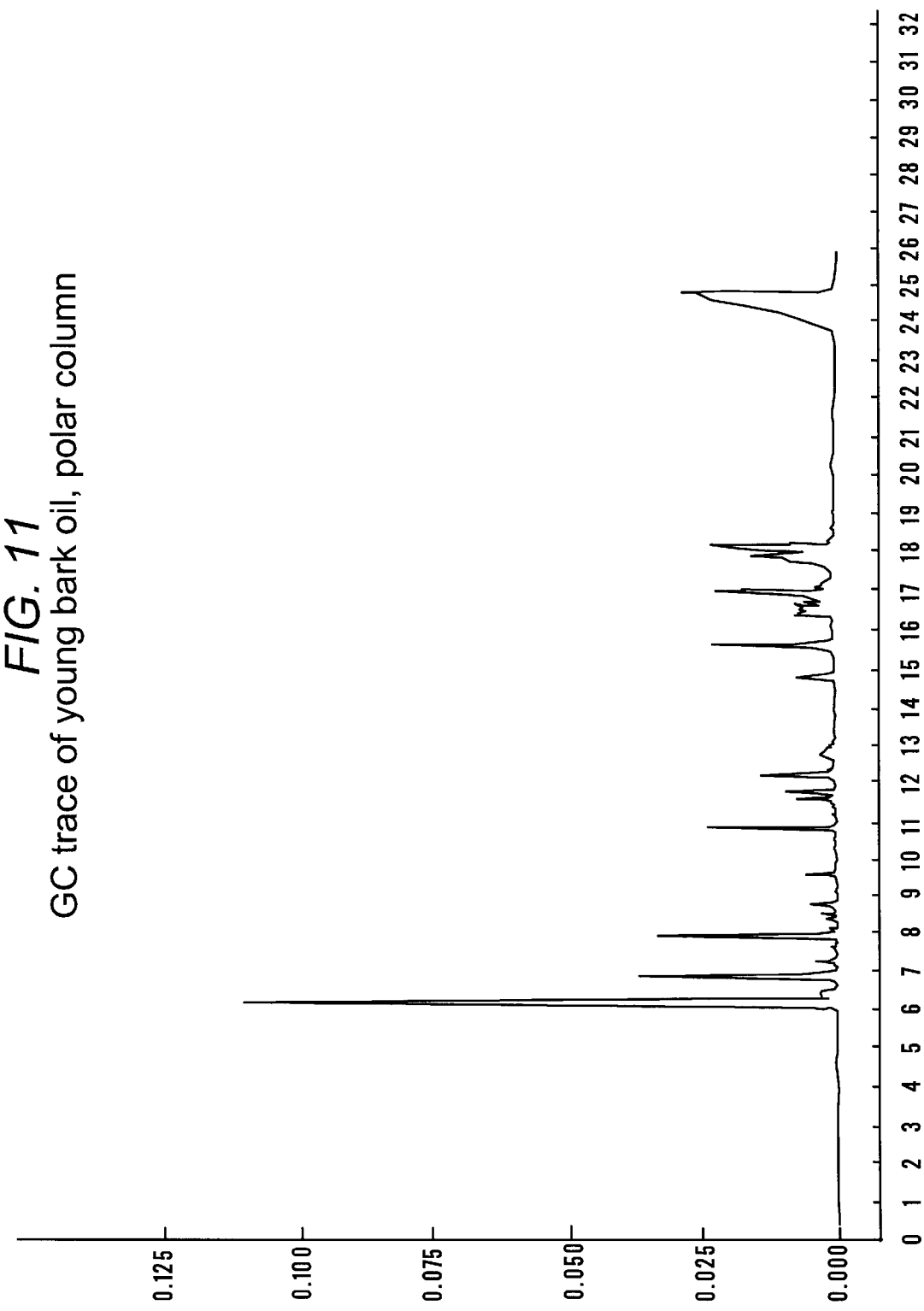

GC trace of young bark oil, non-polar column

GC/MS trace of the young bark oil

GC/MS trace of the old bark oil

Identification of Constituents of Canelo "old" Bark Oil by GC/MS

FIG. 16

| PEAK # | rt | AREA % | COMPOUND |
|---|---|---|---|
| 4 | 11.79 | 2.72 | alpha-Pinene |
| 6 | 12.77 | 1.81 | gamma-3-Carene |
| 17 | 17.77 | 1.20 | Unk |
| 18 | 18.04 | 9.24 | Unk |
| 19 | 18.19 | 15.32 | Unk |
| 20 | 18.33 | 2.00 | Unk |
| 21 | 18.56 | 3.26 | beta-Carophyllane |
| 22 | 18.70 | 3.62 | alpha-Humulane |
| 23 | 18.85 | 2.37 | Unk |
| 24 | 19.14 | 8.09 | beta-Himachalene |
| 25 | 19.49 | 2.04 | trans-beta-Farnasene |
| 26 | 19.60 | 6.37 | alpha-Beramotene |
| 27 | 19.75 | 1.17 | Unk |
| 28 | 19.94 | 7.97 | Benzene,1-(1,5,dimethyl-4-hexenyl)-4-Methyl |
| 33 | 22.01 | 0.78 | Unk |
| 34 | 22.18 | 0.48 | Unk |
| 37 | 33.07 | 2.30 | elemol |
| 38 | 23.19 | 0.65 | beta-Bisabolane |
| 42 | 23.83 | 1.11 | Unk |
| 43 | 23.92 | 6.21 | Unk |
| 46 | 24.17 | 1.98 | beta-Himachalene |
| 48 | 24.38 | 1.23 | gamma-Maalene |
| 47 | 24.67 | 2.33 | Unk |
| 49 | 25.25 | 0.87 | Unk |
| 50 | 25.46 | 0.93 | beta-Eudesmol |
| 51 | 25.92 | 8.14 | Unk |
| 57 | 30.94 | 2.76 | Driminol |

Identification of Constituents of Canelo "YOUNG" Bark Oil by GC/MS

FIG. 18

| PEAK # | rt | AREA % | COMPOUND |
|---|---|---|---|
| 1 | 11.83 | 9.14 | alpha-Pinene |
| 3 | 12.83 | 1.66 | beta-Pinene |
| 6 | 13.82 | 8.96 | Limonene |
| 13 | 17.43 | 2.13 | Linalool |
| 16 | 18.35 | 0.62 | Unk |
| 17 | 18.69 | 1.39 | beta-Carophyllane |
| 20 | 19.20 | 1.44 | 1-alpha-Tarpineol |
| 28 | 22.23 | 2.31 | Farmesol |
| 30 | 23.13 | 14.31 | Elemol |
| 31 | 23.89 | 2.26 | Unk |
| 32 | 24.03 | 2.28 | Unk |
| 33 | 24.21 | 1.30 | Unk/MW216 |
| 34 | 24.42 | 6.95 | gamma-Maalene |
| 35 | 24.67 | 0.98 | Celarene |
| 36 | 24.76 | 0.50 | Unk |
| 39 | 25.32 | 12.79 | Eudesmol |
| 40 | 26.52 | 10.77 | beta-Eudesmol |
| 50 | 31.01 | 17.66 | Driminol |

CANELO PRODUCTS AND METHODS OF MAKING AND USING SAME

RELATED APPLICATIONS

This application claims priority from U.S. Provisional Patent Application No. 60/157,915 filed in Oct. 6, 1999. The entire disclosure of the provisional application is considered to be part of the disclosure of the accompanying application and is hereby incorporated by reference.

FIELD OF THE INVENTION

The present invention is directed to Canelo products and methods for making and using such products. In particular, the present invention is directed to formulations containing extracts derived from the Canelo tree for use as a cleanser, an anti-fungal, anti-yeast and antibacterial agent, as a treatment for toothaches, as a diuretic, as a treatment for vitamin C deficiency, as a hair coloring agent, as an agent to treat acne and ulcers, and as an antipyretic and a pain reducer.

BACKGROUND OF THE INVENTION

The Canelo tree, also known as Winters bark, and formally known as Drymis Winteri, was first discovered by John Winter, a surgeon on the 1576 expedition of Sr. Francis Drake, as a treatment for scurvy. The bark was exported to Europe and named Cortex Winteri as a medicinal antiscrubutan until the late 1800s. In 1956, studies were made resulting in findings that Canelo bark has high concentrations of Vitamin C, tanines, and an oil containing sesquiterpenic lactones and flavonoids. The tree is sacred to the Araucanian Indians and is used in religious ceremonies. The tree itself is a large hardwood that can grow to over 30 feet in height with a trunk diameter exceeding three feet. Its leaves are shiny green on their top side and grayish green on their underside with very aromatic white flowers and small oval black fruits. It is believed that the tree is limited in its geographic locations and is presently found only in southern Chile in a small portion of Argentina.

SUMMARY OF THE INVENTION

One aspect of the present invention relates to the use of Canelo a tree extracts to treat one or more of the following conditions: cleansing of wounds, anti-rheumatic, antiulceretic; elimination of body odors; treatment for chronic infections, in vitro affects against staphylococcus aureus and as a disinfectant. Another aspect of the present invention is the use of extracts from the Canelo tree and formulations for one or more of the following: cosmetics; phytonutrients, natural flavor extracts; and pest repellancy agents.

The present inventor has found that the antiseptic and antibacterial properties of Canelo tree extracts are greater than those of tea tree oil. Moreover, the present inventor has also appreciated that Canelo tree extract also contains bioflavonoids, natural antioxidants and anticarcinogenic properties and therefore, various formulations encompassed by the present invention provide various therapeutic uses.

The present inventor has discovered that formulations of Canelo extract have a significant allomonal biological activity, providing a defense against predators. Thus, one use of the present invention relates to a natural insecticide and pest repellant for use directly in liquid and pellet form, as well as incorporating such material into fiber boards and other building materials for protection against infestation.

Still other aspects of the present invention are the use of compositions comprising Canelo tree extracts which take advantage of such extracts antibacterial activity, antiseptic properties for external bleeding, and for veterinary use for animal skin allergies. When used as a treatment for skin allergies, various irritants naturally found in Canelo tree oil are preferably reduced, diluted and/or eliminated. Yet another use of the present invention is as an emollient for softening skin tissue and to retain moisture in desired tissue. Body cleansers and deodorants comprising extracts from the Canelo tree provide a fresh aroma, as well as a tingly feeling on human skin, thus finding applications as after shower tonics and lotions.

Still further applications of the present invention relate to flavor and perfume uses.

When ingested, extracts from the Canelo tree can also be used to treat various types of fungal, yeast and bacterial infections, and in particular, can be used as an antiulceretic. As a medicinal component, extracts from Canelo tree oil can be used to inhibit certain types of pancreatic cancer.

Extracts from the Canelo tree can be obtained through straightforward distillation processes, but may also be obtained using pressure based processes.

While not bound by theory, it is believed that particular extracts from the Canelo tree contain significant concentrations of the bioflavonoids quercetin and luteolin (which contribute to the maintenance of normal blood vessel conditions by decreasing capillary permeability and fragility, thus finding therapeutic use as a capillary protectant), and furthermore, such bioflavonoids appear to have a synergistic effect with ascorbic acid. Thus, another aspect of the present invention relates to a combination of Canelo tree extract and ascorbic acid.

Another component of Canelo tree extract is Sesamin, believed to have insecticide characteristics and thus, useful in formulating natural products to act as an insect repellant. Such products have a strong allamonal biologic like activity with an inhibition zone of at least about 21 to 30 millimeters, making it useful as a natural industrial insecticide and pest repellant.

A GC/MS analysis of oils present in Canelo bark identify the following compounds: α-Pinene; βPinene; γ3-Carene; Limonene, Linalool, β-Caryophyllene; α-Humulene; β-Himachalene; α-Terpineol; trans-β-Farnesene; α-Beramotene, Benezene; Farnesol; Elemol; β-Bisabolene; γ-Maaliene; Calarene; Eudesmol; β-Eudesmol; Driminol.

Extracts of the Canelo tree are useful as natural antioxidants and thus, useful in the production of natural products for preserving foods. Finally, particular formulations of the present invention comprise extracts from the Canelo tree which find various applications as a cleanser, an anti-fungal, anti-yeast and antibacterial agent, as a treatment for toothaches, as a diuretic, as a treatment for vitamin C deficiency, as a hair coloring agent, as an agent to treat acne and ulcers, and as an antipyretic and a pain reducer

BRIEF DESCRIPTION OF THE DRAWINGS

FIG. 2 shows Table 1 which provides information relating to constituents found in Canelo "young" bark oil.

FIG. 3 shows Table 2 which provides information relating to constituents found in Canelo "old" bark oil.

FIG. 4 shows Table 3 which provides information relating to constituents found in as comparison of bark oils.

FIG. 6 shows a table reflecting constituents of Canelo oil as identified in FIG. 5.

FIG. 7 shows an LC/MS analysis of old Canelo bark extracts.

FIG. 8 shows an LC/MS analysis of young Canelo bark extracts.

FIG. 9 shows GC polar column data relating to old Canelo bark.

FIG. 10 shows GC non-polar column data relating to old Canelo bark.

FIG. 11 shows GC polar column data relating to young Canelo bark oil.

FIG. 16 is a table that provides information concerning the GC/MS peaks as depicted in FIG. 15.

FIG. 18 is a table that provides information concerning the GC/MS peaks as depicted in FIG. 17.

DETAILED DESCRIPTION OF THE PREFERRED EMBODIMENT

Figure 1A:
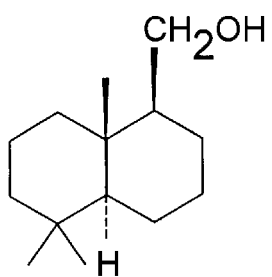
FIGS. 1A–R depict chemical structures of identified compounds in Canelo oil.

Chemical Extraction of Drimys Winteri (Canelo) Procedure

An extraction was carried out with ethanol (2×5 L) on 2 kg of Canelo leaves using a filter. The mixture was distilled to dryness, giving 430 g of product, to which was added hot water to give a precipitate of lipids and chlorophyll. The precipitate was filtered and the aqueous solution was extracted with chloroform using a separation funnel. This solution was distilled to dryness, which gave the chloroform extract. Then, on a second extraction, ethyl acetate was added to the aqueous solution left behind in the separation funnel to give the ethyl acetate extract. Finally, the remaining of the aqueous solution was extracted with amyl alcohol, giving the amyl extract.

Chloroform Extract

This extract was subjected to silica gel column chromatography, using solvents with increasing polarities, allowing us to isolate and identify the following sesquiterpenic lactones.

With respect to the procedures for extracting particular components from the bark of Canelo trees, steam distillation processees and solvent an extraction of young tree bark and old tree bark was performed. 28.5 Kg of "young" tee bark and 27.0 Kg of thick "old" tree bark were used in the following below described processees.

Method

Steam distillation: About 200 grams of each bark type, cut to an accommodating size (0.5 in²), were placed in a 3-L round bottom flask. About 1.5-L of DI $H_2O$ was added, enough to cover the bark. The water was boiled overnight 919 hours for the young bark and 16 hours for the old bark) and the steam distillate was collected in an apparatus suitable to collect oils lighter than water.

The oil was removed by pipette and analyzed by gas chromatography (Gc) and gas chromatography-mass spectrometry (GC/MS).

Soxhlet Extractions with Bexane, Ethyl Acetate and Methanol

Old Bark: About 200 grams of bark was loaded into a large soxhlet and 3-L of hexane added to the 5-L flask. The soxhlet extraction lasted for 8.0 hours and the hexane extract was evaporated to a greenish golden oil yielding 10.9 grams solids. The same bark was extracted again using 3-L of ethyl acetate for 7.5 hours. The ethyl acetate extract was evaporated to a dark yellow solid and yielded 9.0 grams. The same bark was extracted a third time using 3-L of methanol for 27.5 hours. The methanol extract was evaporated to a light brown solid yielding 27.5 grams.

Young Bark: About 200 grams of bark was loaded into a large soxhlet and 3-L of hexane added to the 5-L flask. The soxhlet extraction ran for 7.5 hours and the hexane extraction was evaporated to a yellow/green oil yielding 8.87 grams solids. The same bard was then extracted using 3-L of ethyl acetate for 8.5 hours. The ethyl acetate extract was evaporated to a yellow/green solid yielding 9.8 grams. The same bark was extracted a third time using 3-L of methanol extracting for 22.25 hours. The methanol extract was evaporated to a brown green solid and yielded 02.97 grams.

Materials/Apparatus:

Oil lighter than water collection apparatus: collects up to 30 ml

Large Soxhlet apparatus w/5-L flask

Starting material: Canelo bark, Drymis Winteri Forst.
　Young bark 28.5 Kg (dry wt.)
　Old bark 27.0 Kg Solvents:

DI water

Hexanes—reagent grade

Ethyl acetate—reagent grade

Methanol—technical grade

Analytical:

GC:
　Equipment: Varian star 3400
　Method: Oils were analyzed on both polar and non-polar columns, injected neat.

GC/MS:

Equipment: Hewlett Packard 5971a, HP5890-GC

Library: NBS and Wiley

Method: Oils analyzed on a polar column at 1:100 and 1:1000 dilutions.

Results:

1) Steam distillate of Canelo bark:
　Starting material 200 grams of each bark type.

|  | Yield | % Yield (w/w) |
| --- | --- | --- |
| Young bark | 2.40 g/2.7 ml | 1.2% |
| Old bark | 6.44 g/7.5 ml | 3.2% |

2) Solvent extractions of the Canelo bark:

| Solvent | Yield | % yield (w/w) | Appearance |
|---|---|---|---|
| Young bark: | | | |
| Hexane | 8.87 grams | 4.4% | yellow green oil |
| Ethyl acetate | 9.8 grams | 4.9% | dark tan/green solid |
| Methanol | 20.97 grams | 10.5% | tan green solid |
| Old bark: | | | |
| Hexane | 10.9 grams | 5.5% | greenish yellow oil |
| Ethyl acetate | 9.0 grams | 3.6% | dark yellow solids |
| Methanol | 27.5 grams | 13.8% | light brown solid |

Discussion:

The steam distilled oils were analyzed on both polar and non-polar columns on the GC to determine the best method of analysis. The polar column gave a better separation.

The polar column was used for analyzing the Canelo oils on the GC/MS. The peak numbers were determined by lowering the sensitivity to 0.25% area abundance. The peaks chosen for identification were all over 0.5% area abundance. These peaks are marked on the GC/MS traces. Peak identifications were chosen from the libraries listed in the analytical section. FIGS. 2–4 contain data of the bark constituents along with peak retention times and percent area abundance.

Chemical Extraction of Drimys Winteri (Canelo)

Procedure: The extraction was carried out with ethanol (2×5 L) on 2 kg of canelo leaves using a filter. The mixture was distilled to dryness, giving 430 g of product, to which we added hot water to give a precipitate of lipids and chlorophyll. The precipitate was filtered and the aqueous solution was extracted with chloroform using a separation funnel. This solution was distilled to dryness, which gave the chloroform extract. Then, on a second extraction, ethyl acetate was added to the aqueous solution left behind in the separation funnel to give the ethyl acetate extract. Finally, the remaining of the aqueous solution was extracted with amyl alcohol, giving the amyl extract.

Chloroform Extract: This extract was subjected to silica gel column chromatography, using solvents with increasing polarities, allowing us to isolate and identify the following sesquiterpenic lactones.

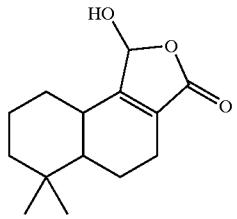

Valdiviolide

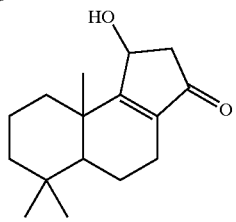

Fuegin

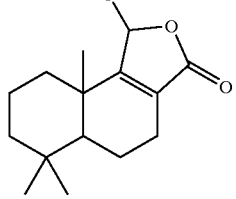

Winterin

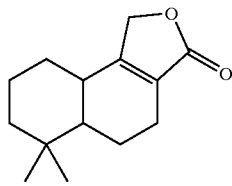

Confertifoline

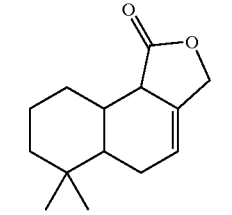

Drimenine

The chloroform extraction of canelo bark gave the following further lactones: futronolide and drimenol.

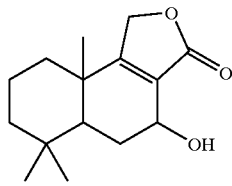

Futronolide

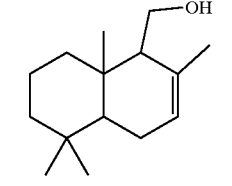

Drimenol

The anticarcinogenic activity found in canelo must be due to Valdiviolide, fuegine, confertifoline and futronollide through DNA blocking via π complexes

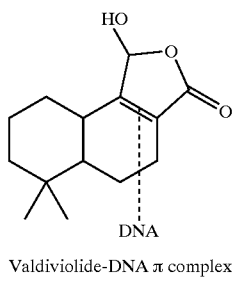

Valdiviolide-DNA π complex or by enzyme deactivation of t-RNA aminoacylsynthetase which carries out protein biosynthesis.

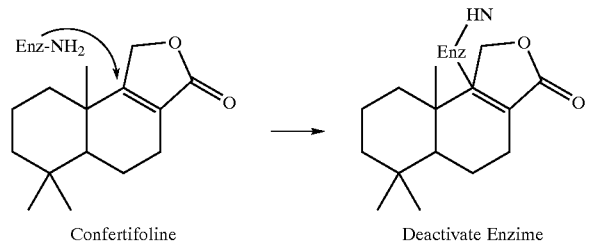

Confertifoline      Deactivate Enzime

Since there are no protein synthesis the sick cell dies, as well as healthy ones, but in less quantity.

Steam Distillation. Steam distillation of canelo bark allowed the identification of the following sesquiterpenes: drimenol, drimene, valdiviolide, α-chamigrene and a hydrocarbon which we were unable to identify.

Drimenol found in the oil performs the same function as ethyl alcohol, that is, works as a disinfectant (because it is an alcohol). The feeling of freshness to the skin is due to the oily properties and volatilities of drimene, α-chamigreno and the unknown hydrocarbon. Valdiviolide, also present in the essential oil, has a structure with anticarcinogenic properties and should be repellant to inserts.

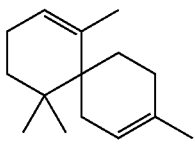

α-Chamigrene

Ethyl Acetate Extract: Cellulose column chromatography allowed us to identify the following flavonoids; quercetin-3-O-galactoside and taxifoline.

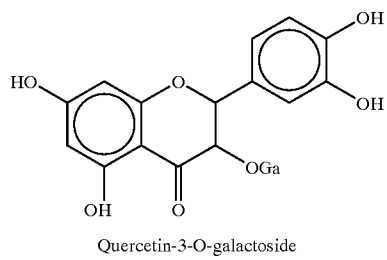

Quercetin-3-O-galactoside

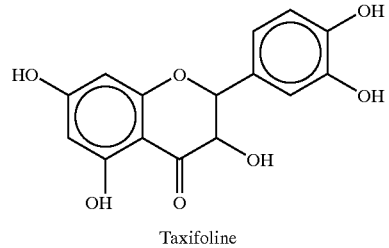

Taxifoline

From the application viewpoint the most important of these two flavonoids is taxifoline since it has shown anti-carcinogenic activity on P-388 cultures (leufocytic leukemia). Also taxifoline should show antioxidant activity since when faced to any biological generator of free radicals (like riboflavine), taxifoline will produce hydrogen free radical which would neutralize peroxides coming from atmospheric oxygen.

Amyl Extract: Using cellulose column chromatography we isolated quercetine and isoramnetine, both being flavonoids.

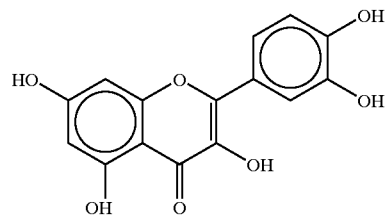

Quercetin

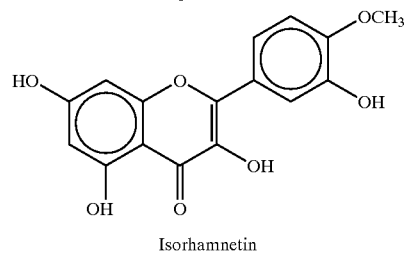

Isorhamnetin

No alkaloids whatsoever were found in any of the extractions performed. On the other hand, chromatographic comparison (thin layer chromatography) of the wood and bark extract gave exactly the same result, meaning that both have the same chemical composition.

Biological Activity: Solutions of chloroform extracted stems and leaves show biological activity on p-388 (linfocitic leukemia) and KB human nasal pharynx carcinoma. This activity is thought to be due to the presence of sesquiterpenic lactones as confertfoline, Valdiviolide, etc., which very likely block DNA so that metabolism is inhibited. The canelo allomonal activity (defense against predators) is though to be due to these compounds. This extract also showed antimicotic activity against Sarcina lutea (+++) and Staphilo coccus aureus (+++).

+=small inhibition zone of 8–10 mm.
++=inhibition zone of 11–20 mm.
+++=inhibition zone of 21–30 mm.
++++=inhibition zone bigger than 30 mm.

Figure 1B:
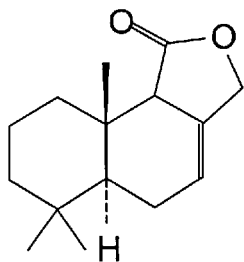
Figure 1C:
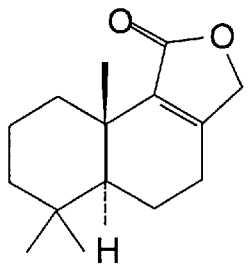
Figure 1D:
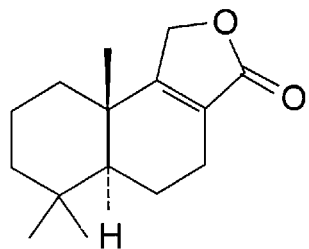
Figure 1E:
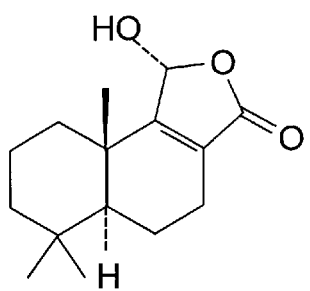
Figure 1F:
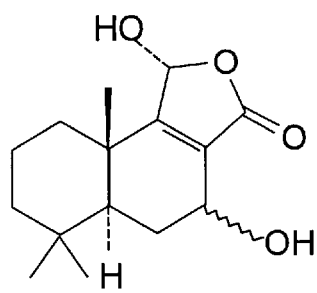
Figure 1G:
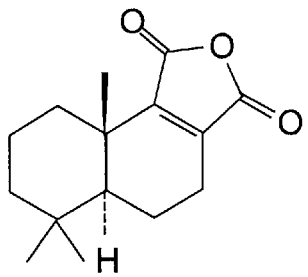
Figure 1I:
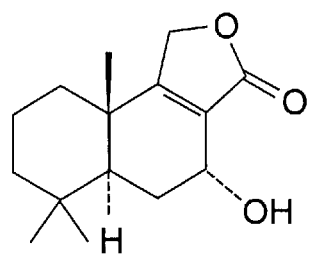
Figure 1J:
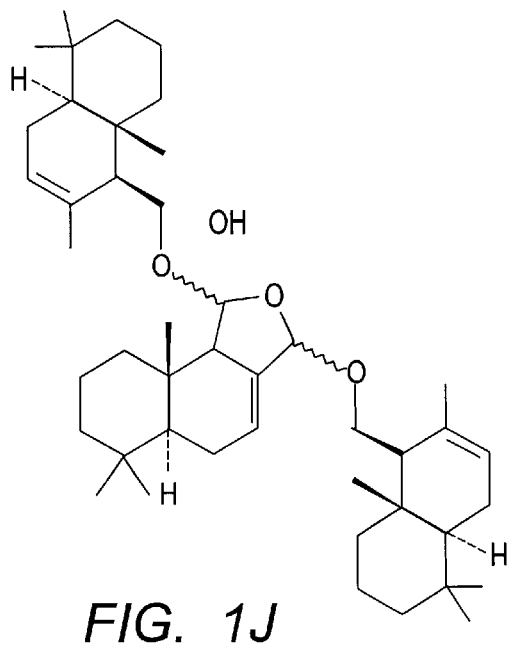
Figure 1K:
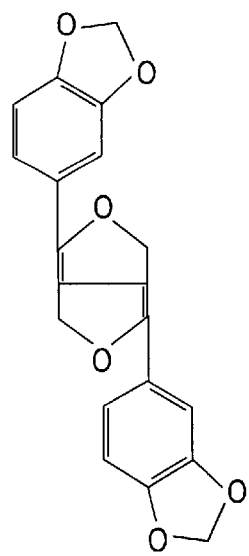
Figure 1L:
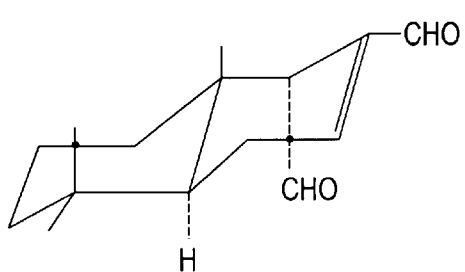
Figure 1M:
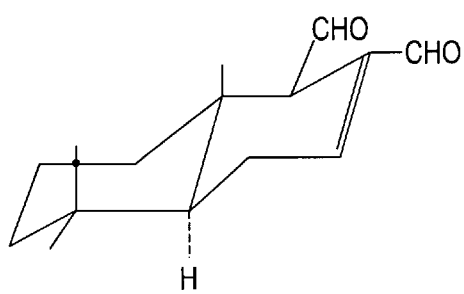
Figure 1N:
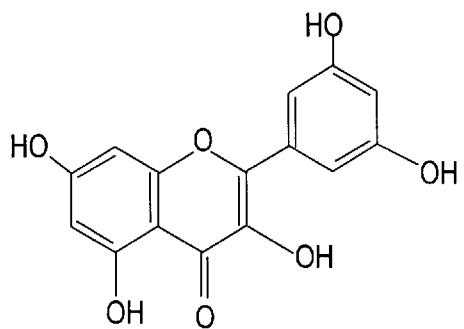

Moreover, the "Canelo" bark extracted with petroleum ether and further elimination of the solvent, was extracted with methanol which was evaporated to dryness, then was subjected to silica gel column chromatography allowing the isolation of:

drimenin (FIG. 1B)

drimerol (FIG. 1A)

sesamin (which acts as insecticide synergistic, skin softener, and veterinary use against animals parasite) (FIG. 1K)

vadiviolide (FIG. 1E)

epi-poligodial (FIG. 1L)

poligodial (FIG. 1M)

Figure 1O:
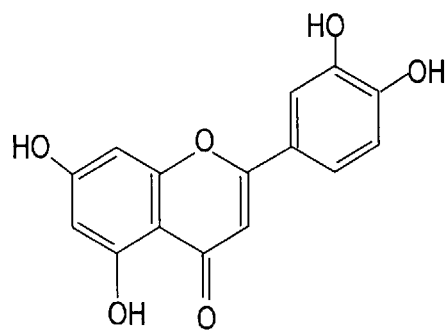

Further work on the Canelo leaves allowed the isolation and identification of:

a sesquiterpenic lactone: Criptomeridiol.

and the following flavonoids:

Quercetin (FIG. 1M) and Luteolin (FIG. 1O) (bioflavonoids, which contribute to the maintenance of normal blood vessel conditions by decreasing capillary permeability and fragility. Thus, its therapeutic use as capillary protectant is recommended). It also shows synergistic effect with ascorbic acid.

Figure 1P:
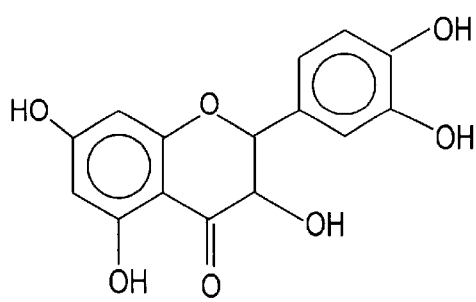
Figure 1Q:
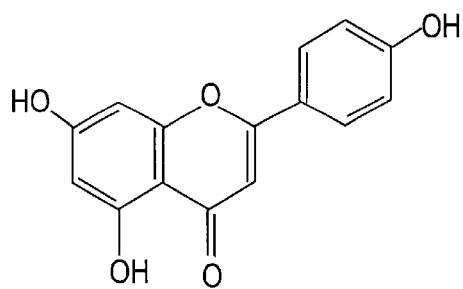
Figure 1R:
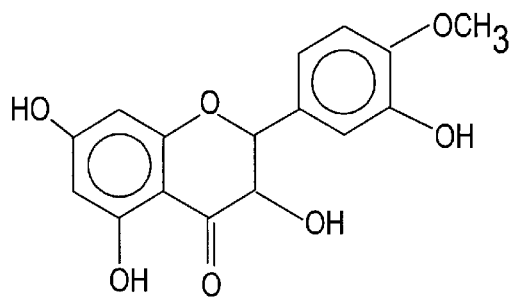
Figure 5:
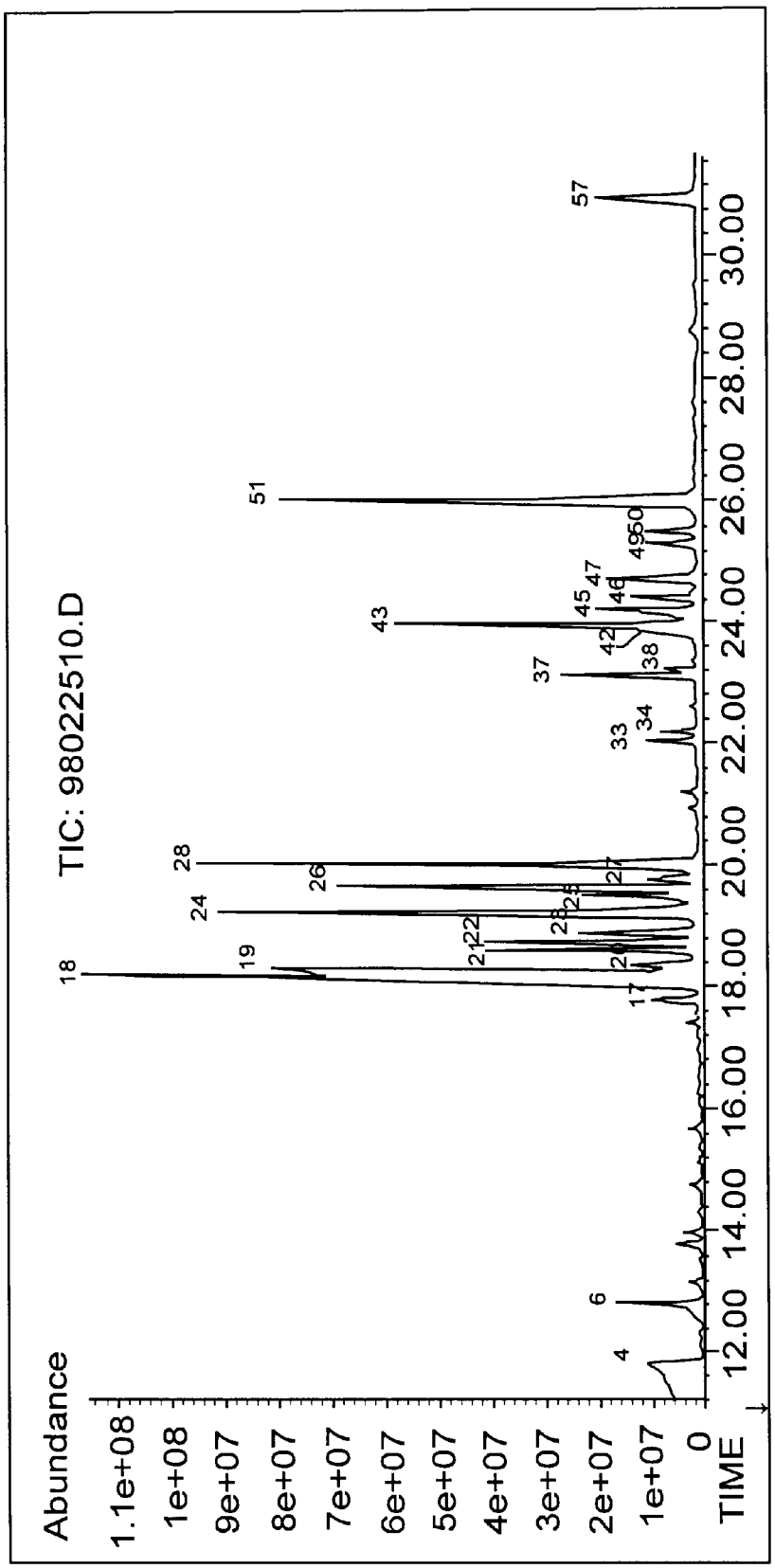
FIG. 5 shows GC/MS data that identifies constituents of Canelo "old" bark oil.
Figure 12:
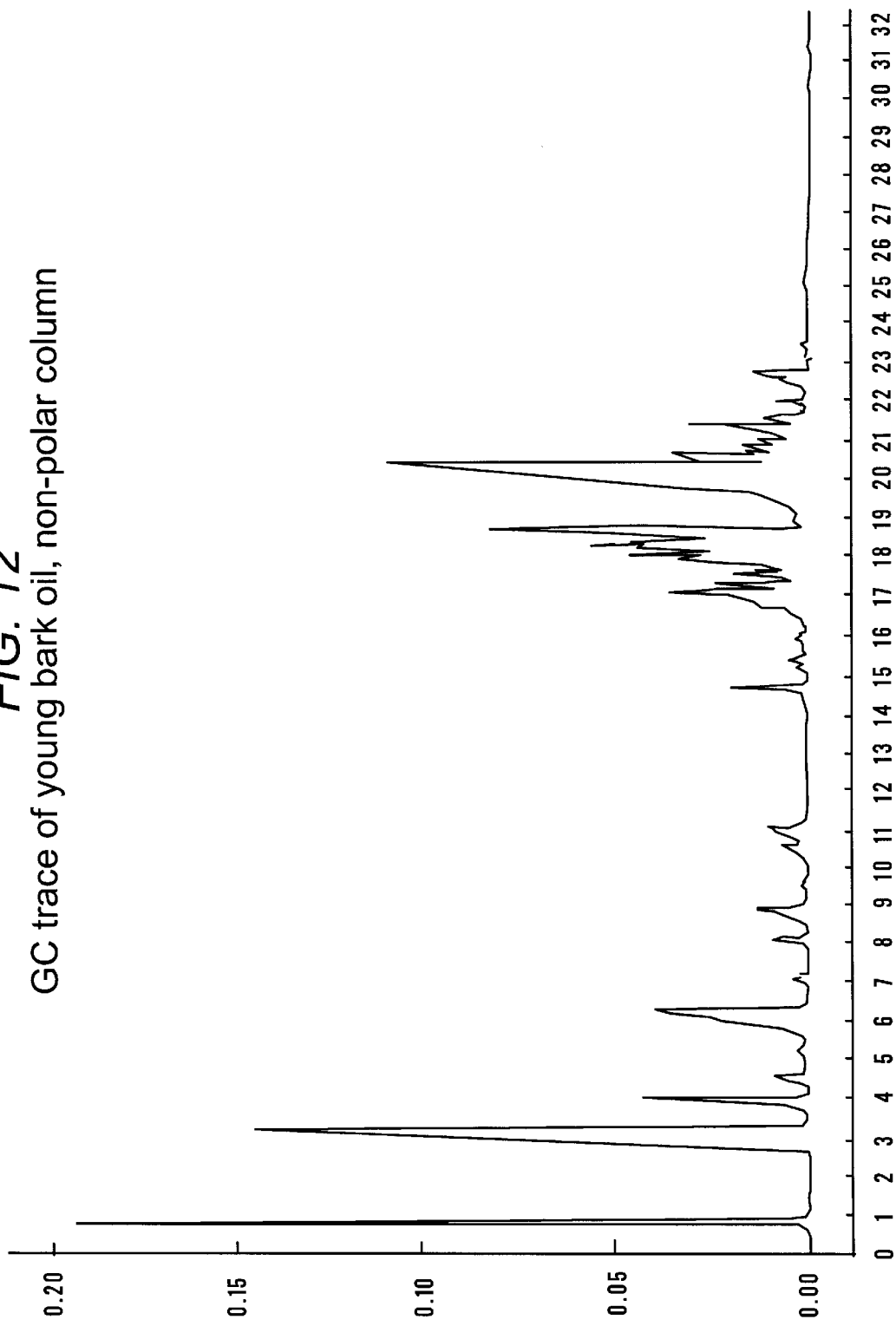
FIG. 12 shows GC non-polar column data relating to young Canelo bark oil.
Figure 13:
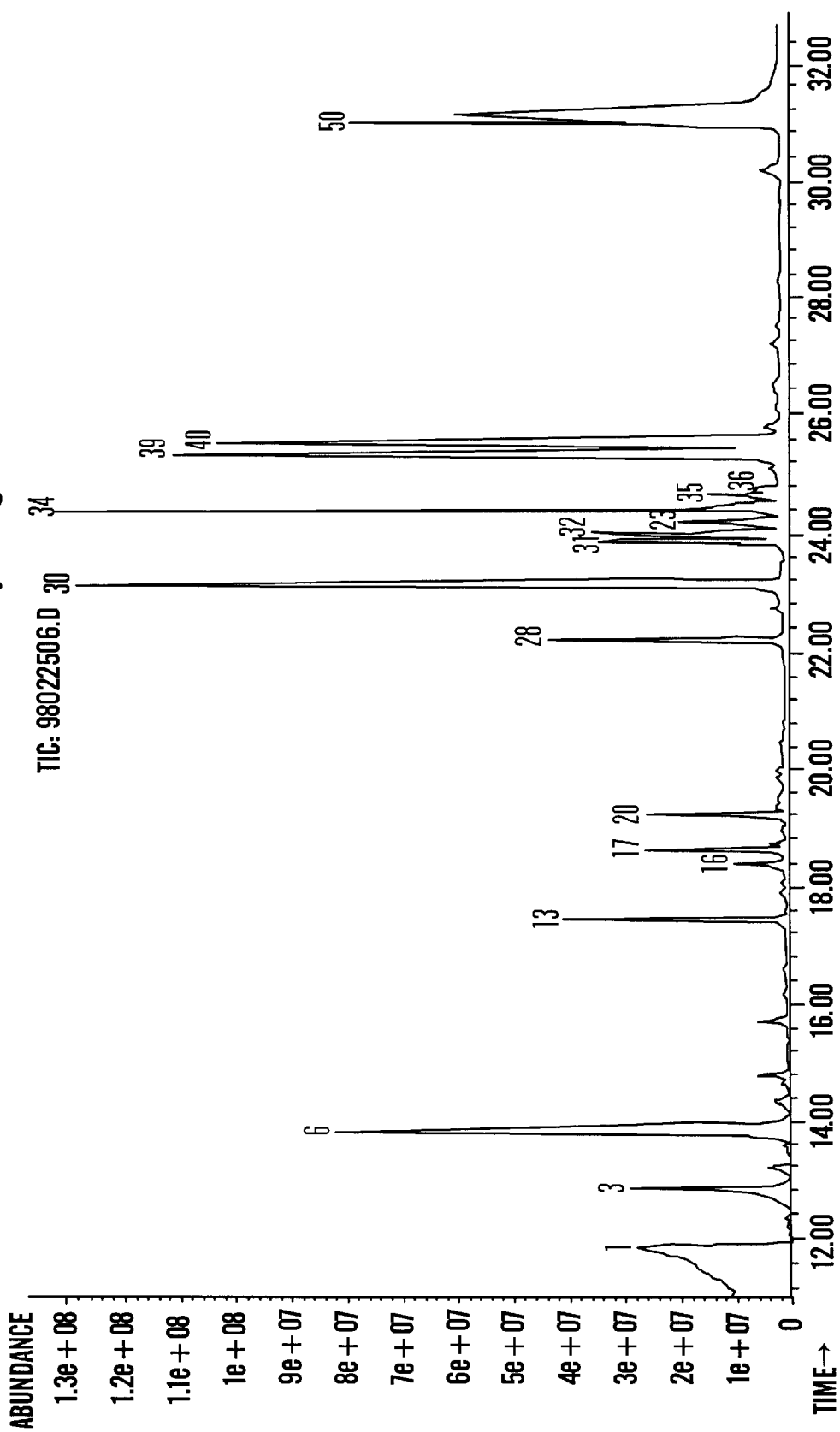
FIG. 13 shows GC/MS data relating to young Canelo bark oil.
Figure 14:
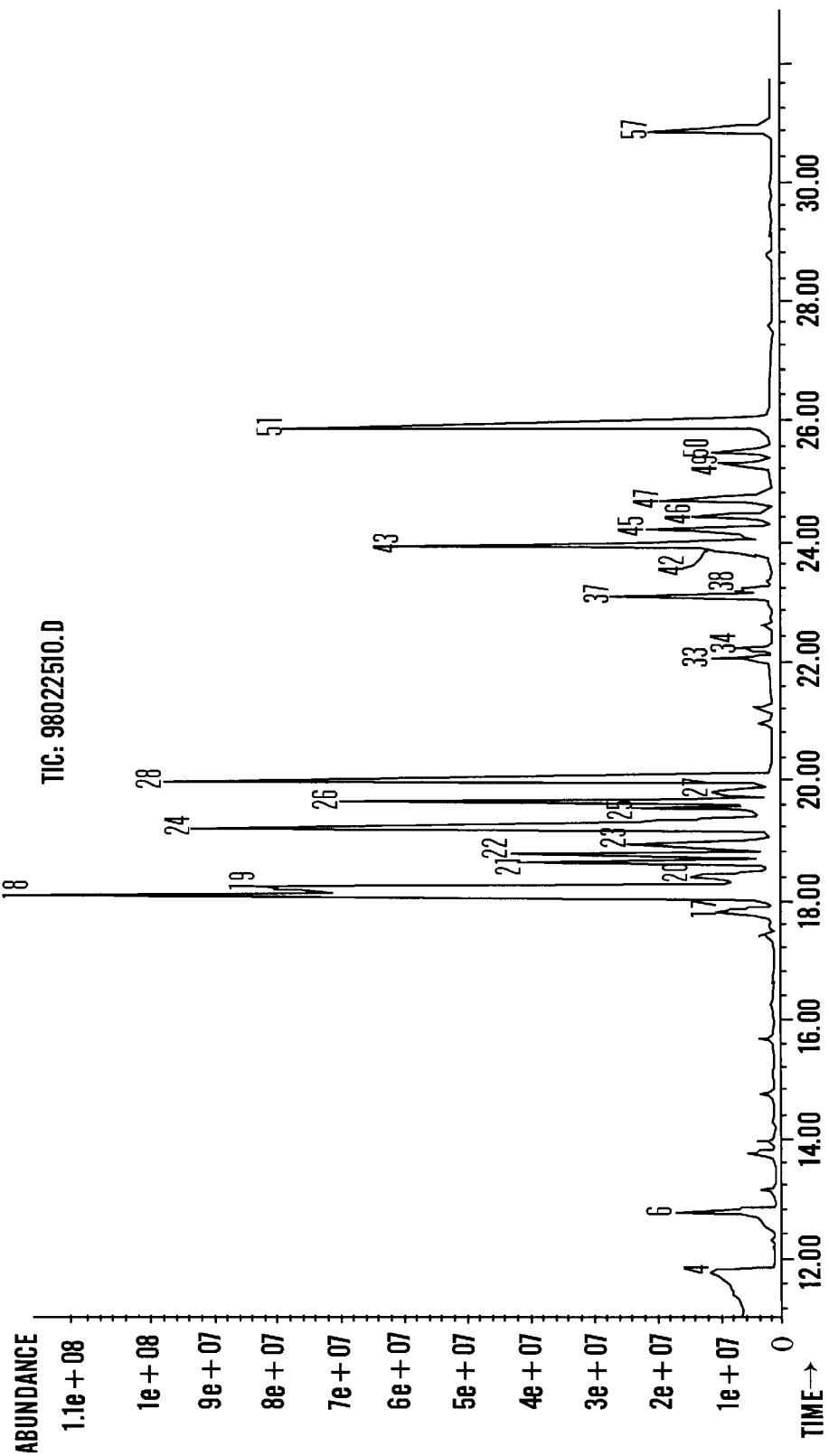
FIG. 14 shows GC/MS data relating to old Canelo bark oil.
Figure 15:
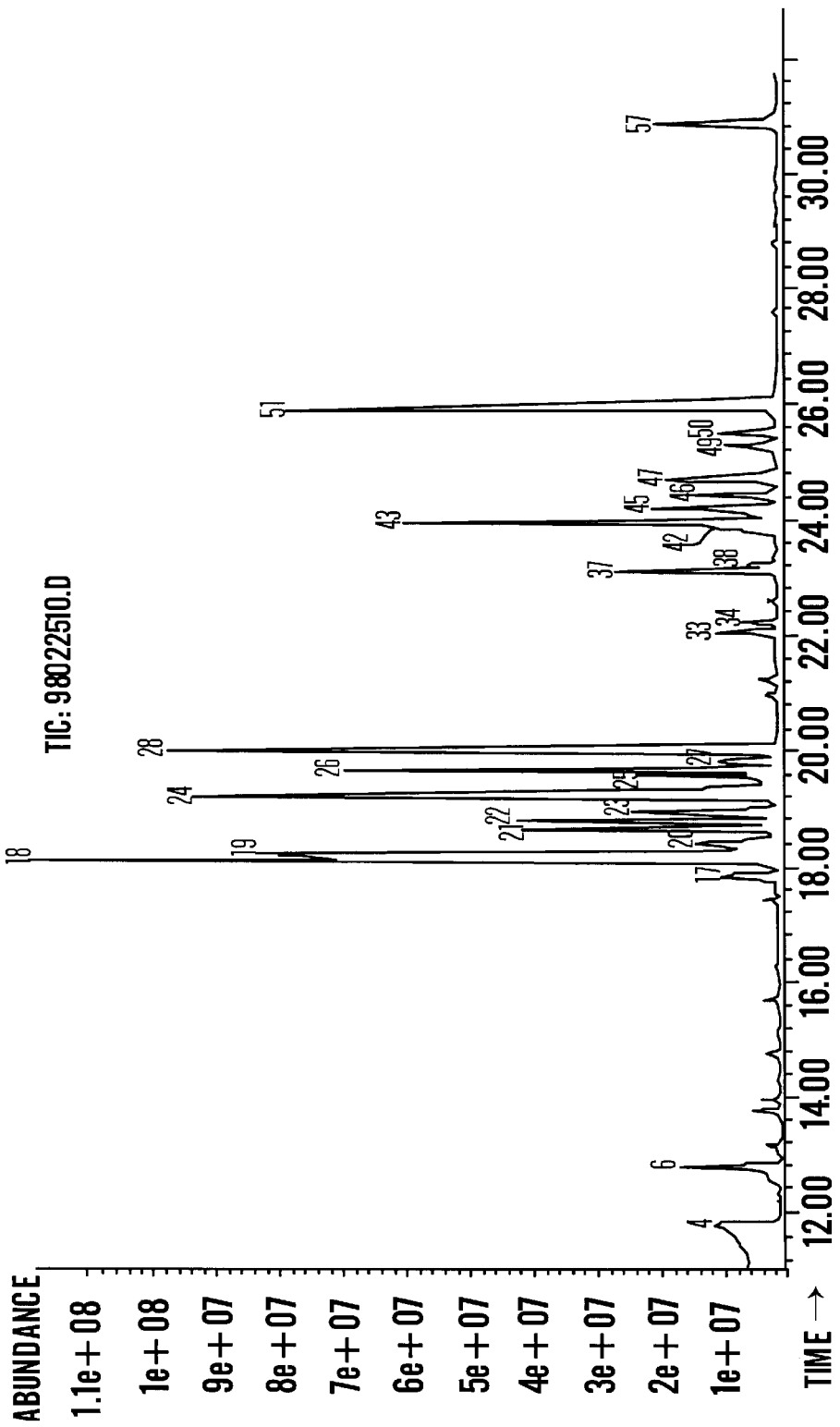
FIG. 15 shows GC/MS data relating to the identification of constituents found in old Canelo bark oil.
Figure 17:
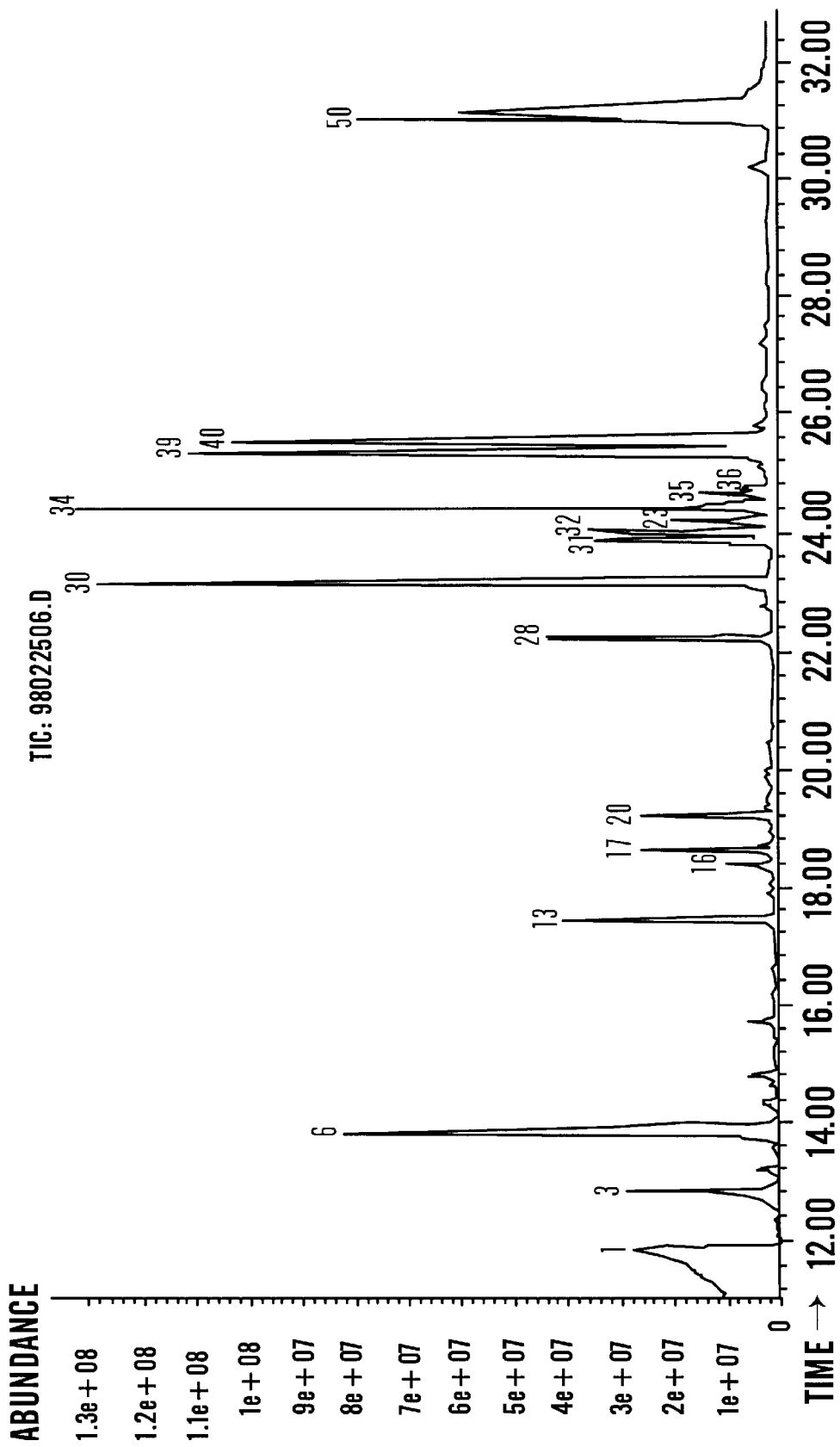
FIG. 17 shows GC/MS data relating to the identification of constituents found in young Canelo bark oil.
Figure 19A:
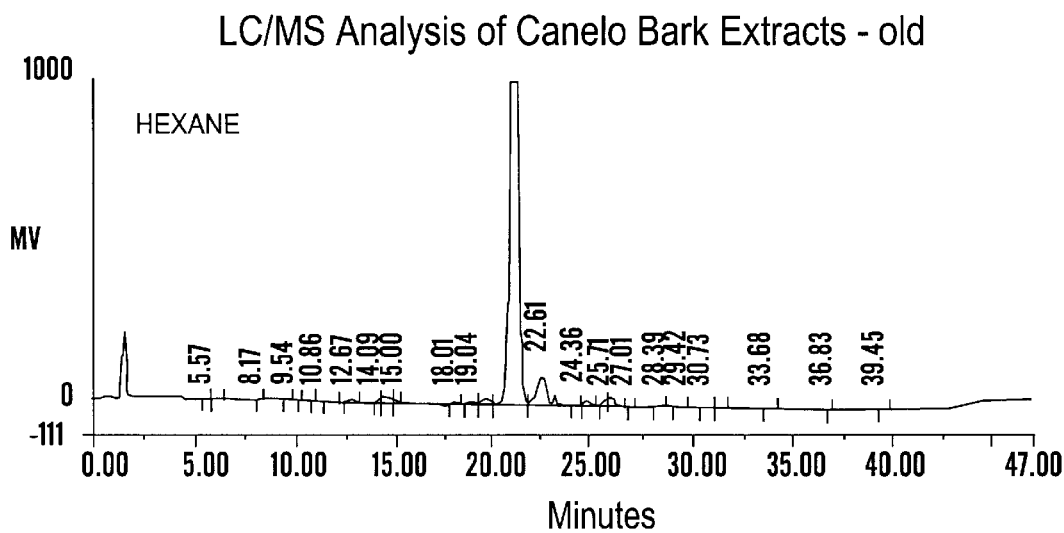
FIGS. 19A–C depict LC/MS analysis of old Canelo bark extracts.
Figure 19B:
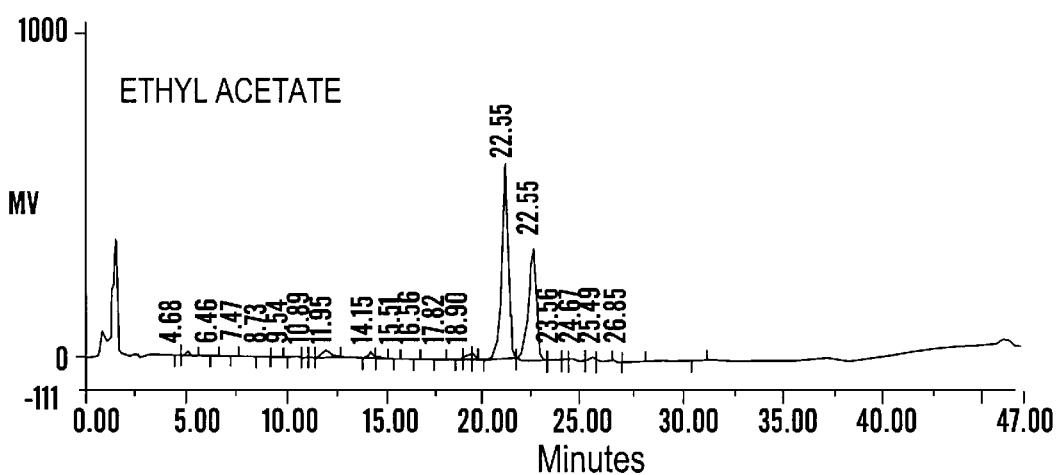
Figure 19C:
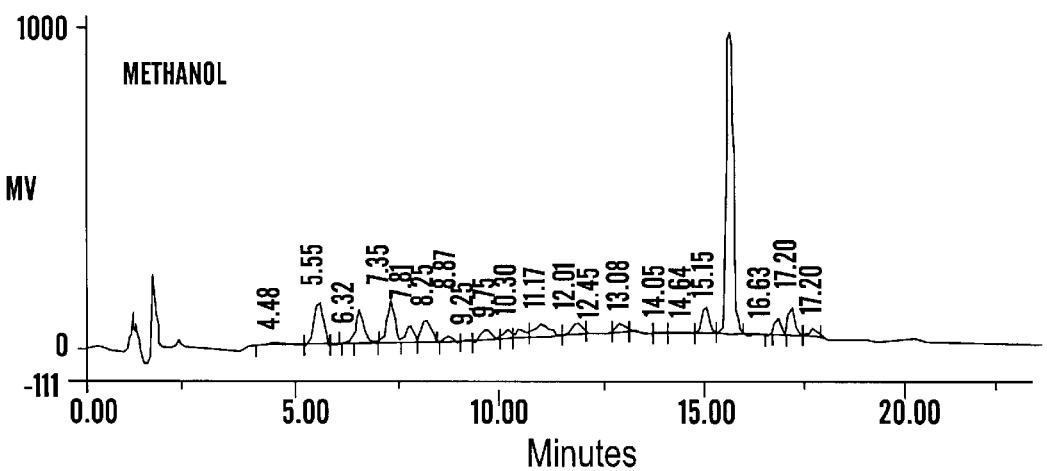
Figure 20A:
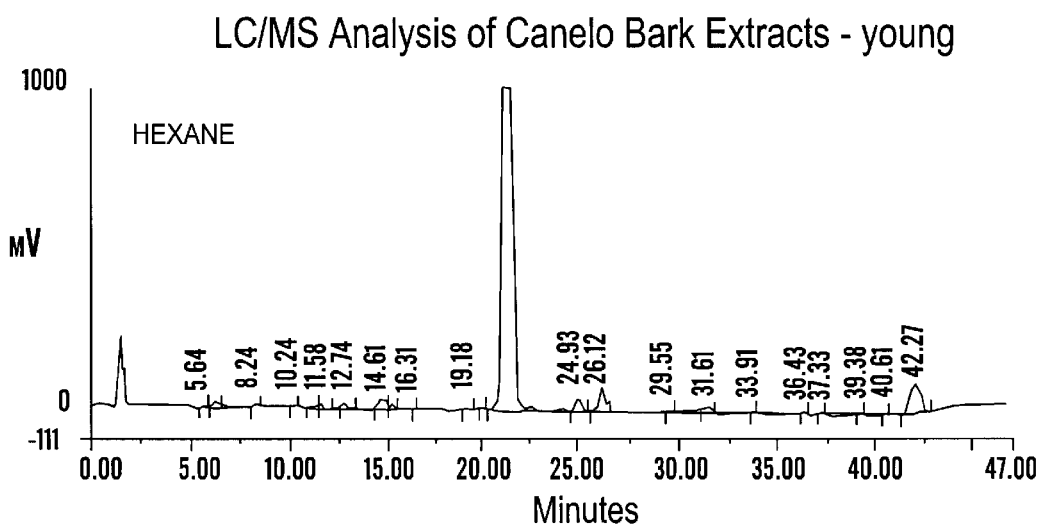
FIGS. 20A–C depict LC/MS analysis of young Canelo bark extracts.
Figure 20B:
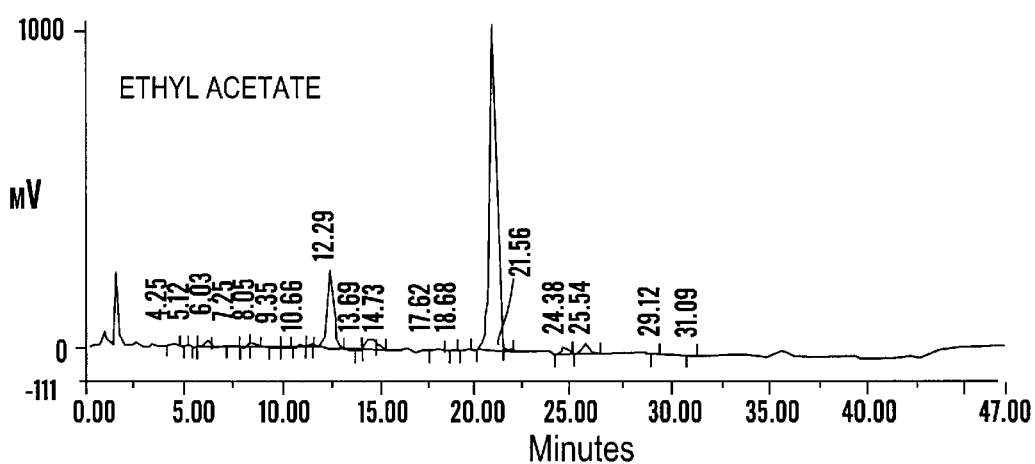
Figure 20C:
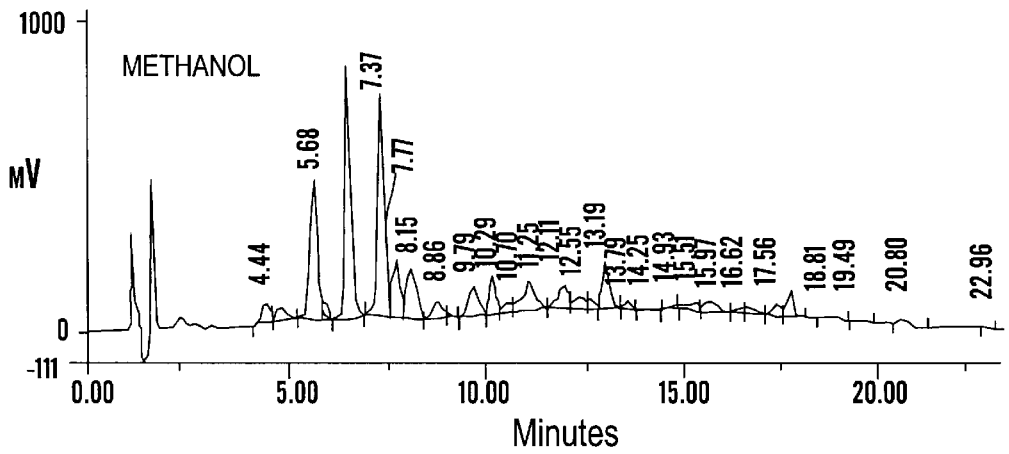

| Taxifolin (FIG. 1P) | Astilbin |
| Quercetrin | Kamferol |
| Cirsimaritin | Apigenin (FIG. 1Q) |
| Isorhamnetin (FIG. 1R) | |

Extracted (by steam distillation) canelo oil from canelo bark was injected through a chromatographer HP-5690 Series II-Mass detector 5972 with a 25 meter HP ULTRA II column.

The chromatogram shows two groups of components:

about 20 chemical components in large proportion, and about 60 chemical components in smaller proportions.

We have also obtained three fractions, namely:

ethanol extract, methanol extract, water extract

Oils/Extracts Yields

| | Yield | % Yield (w/w) |
|---|---|---|
| Young Bark Oil | 2.40 g/2.7 ml | 1.2 |
| Old Bark Oil | 6.44 g/7.5 ml | 3.2 |
| Young Bark Extracts | | |
| Hexane | 8.87 g | 4.4 |
| Ethly Acetate | 9.80 g | 4.9 |
| Methanol | 20.90 g | 10.5 |
| Old Bark Extracts | | |
| Hexane | 10.9 g | 5.5 |
| Ethyl Acetate | 9.0 g | 3.6 |
| Methanol | 27.5 g | 13.8 |

While various embodiments of the present invention have been described in detail, it is apparent that further modifications and adaptations of the invention will occur to those skilled in the art. However, it is to be expressly understood that such modifications and adaptations are within the spirit and scope of the present invention.

The canelo tree derived products as discussed herein, are also variously referred to as "ushq'tta" and in one embodiment, the present invention utilizes ushq'tta essential oil in various products, including candles, air fresheners, air filters, pest repellants, body deodorants, therapeutic compounds and building materials. To further describe and provide enabling uses of ushq'tta essential oil, the following characteristics are further identified:

appearance: clear, light yellow, viscous liquid boiling point: certain fractions start to boil at 155° C.

stability: stable under ordinary conditions of use and storage

An effective amount of ushq'tta extract for use with any of the applications referred to herein will obviously vary depending upon such applications. In general, however, topical application of an ushq'tta compound is preferably accomplished by using a concentration of at least 1%, more preferably at least 2% and most preferably, at least 5%, with the remaining constituents being suitable emollients, creams, lotions and cleaning agents (e.g., soap, detergents, etc.).

With respect to an application using the ushq'tta extract as a pest repellent agent, similar concentrations as described above are deemed sufficient. In some applications, however, higher strength concentrations, such as at least about 20% of an overall pest repellency agent, consists of ushq'tta extract.

In an application which utilizes the ushq'tta extract as a therapeutic compound in combination with ascorbic acid, preferably at least 10% of such compound comprises ushq'tta extract, more preferably about 25% and most preferably at least about 40%. The amount of ascorbic acid in such formulation is preferably at least about 2%, more preferably at least about 5% and most preferably at least about 8%.

Finally, building materials comprising extracts of ushq'tta have an effective amount of ushq'tta extract so as to act to repel insects. In a preferred embodiment, at least about 1% of a drywall formulation, for example, is comprised of ushq'tta extract, such amount being deemed effective to repel insects. Ushq'tta oil extract can be mixed with plywood and/or particle board formulations to prevent termites from being attracted thereto, such concentrations being generally in the same range (e.g., at least about 1%, more preferably, at least about 5%, and most preferably, at least about 15%).

What is claimed is:

1. A building material comprising an extract derived from a Canelo tree included within a drywall formulation in an amount of at least 1% by weight of said formulation, whereby said Canelo tree extract is effective to repel insects from drywall manufactured using said formulation.

2. A building material, consisting essentially of a board selected from the group consisting of a plywood board and a particle board, said board having at least about 5% by weight of a Canelo tree extract added thereto during the manufacture of said board.

* * * * *